Figure 1:
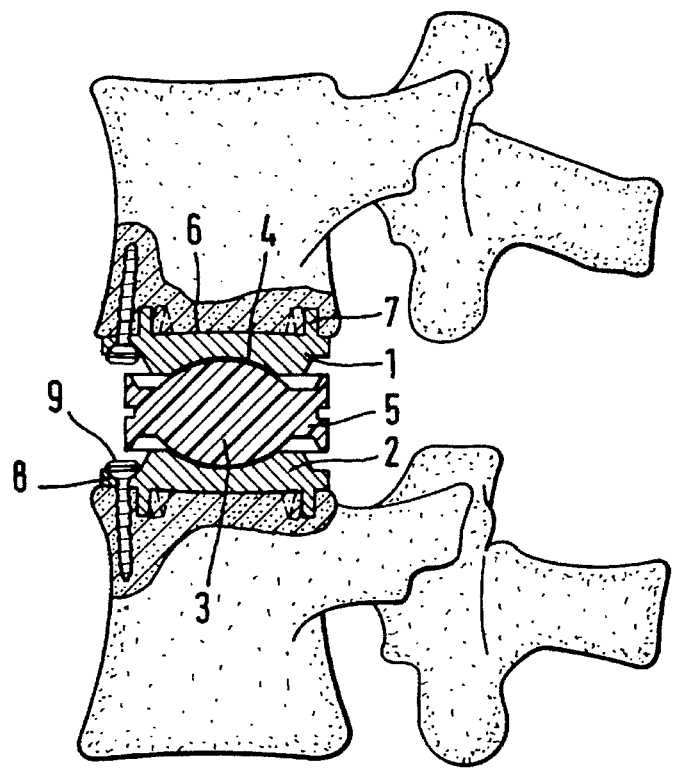

United States Patent [19]

Büttner-Janz

[11] Patent Number: 5,556,431
[45] Date of Patent: Sep. 17, 1996

[54] INTERVERTEBRAL DISC ENDOPROSTHESIS

[76] Inventor: Karin Büttner-Janz, Reetzer Weg 63, 0 - 1144 Berlin, Germany

[21] Appl. No.: 287,701

[22] Filed: Aug. 9, 1994

Related U.S. Application Data

[63] Continuation of Ser. No. 28,978, Mar. 10, 1993, abandoned.

[30] Foreign Application Priority Data

Mar. 13, 1992 [DE] Germany .................. 42 08 115.7

[51] Int. Cl.⁶ ............................................ A61F 2/44
[52] U.S. Cl. ................................... 623/17; 606/61
[58] Field of Search ......................... 623/16, 17, 18; 606/61

[56] References Cited

U.S. PATENT DOCUMENTS

| | | | |
|---|---|---|---|
| 4,636,217 | 1/1987 | Ogilvie et al. | 623/17 |
| 4,759,769 | 7/1988 | Hedman et al. | 623/17 |
| 5,062,850 | 11/1991 | MacMillan et al. | 623/17 |
| 5,147,361 | 9/1992 | Ojima et al. | 623/17 |

FOREIGN PATENT DOCUMENTS

| | | | |
|---|---|---|---|
| 41737B | 4/1986 | Austria. | |
| 0176728A1 | 8/1985 | European Pat. Off. . | |
| 0176728 | 4/1986 | European Pat. Off. | 623/17 |
| 0298233 | 1/1989 | European Pat. Off. . | |
| 0392076A1 | 10/1990 | European Pat. Off. . | |
| 2654226A1 | 9/1991 | France . | |
| 3023353C2 | 4/1981 | Germany . | |
| 8807485 | 8/1989 | Germany . | |
| 3911610A1 | 10/1990 | Germany . | |
| 1505537 | 9/1989 | U.S.S.R. . | |
| 1533685 | 1/1990 | U.S.S.R. . | |

OTHER PUBLICATIONS

German Search Report DE-P 42 08 115.7.
Karin Büttner–Janz, K. Schellnack, H. Zippel. Eine Alternative Behandlungsstrategie beim lumbalen Bandscheibenschaden . . . Z. Orthop. 125 (1987): 1–6.

Primary Examiner—David Isabella
Attorney, Agent, or Firm—Chilton, Alix & Van Kirk

[57] ABSTRACT

An intervertebral disc endoprosthesis which is to be inserted between two vertebrae and has a bottom plate and a top plate which are to be connected to the endplates, facing them, of the vertebrae additionally has screw fastening facilities in order to increase the security of retention of the prosthesis. These screw fastening facilities are formed, for example, by in each case at least one borehole which runs essentially at right angles to the plane of the bottom or top plate and through which a bone screw can be inserted. The center of articulation of the prosthesis is displaced towards the rear relative to the center of the vertebral endplates in order to achieve a more favorable course of the force and, at the same time, to provide space in the ventral edge area to receive the bone screws.

7 Claims, 2 Drawing Sheets

INTERVERTEBRAL DISC ENDOPROSTHESIS

This is a continuation of application Ser. No. 08/028,978 filed on Mar. 10, 1993, now abandoned.

The invention relates to an intervertebral disc endoprosthesis which is to be inserted between two vertebrae and has a bottom plate and a top plate, where the bottom and/or the top plate are provided with facilities to receive at least one bone screw.

In known intervertebral disc endoprostheses, teeth or projections are provided on the outer sides, which face the vertebrae, of the plates and penetrate into the surface of the vertebrae and thus fix the prosthesis in the intervertebral space (EP 176 728 A1; brochure "LINK Zwischenwirbelendoprothese Modell SB-Charité" of W. Link, 1988; FR-A-2659226). In general, this suffices even when the intervertebral spaces open towards the front in a wedge shape as a result of increased lordosis. However, there are cases in which the effectiveness of the teeth is impaired, for example if corrugation or curvature of the endplates of the vertebrae prevents the teeth from penetrating sufficiently. In place of the fixing by means of teeth, it is known to provide on the ventral edge of the prosthesis some brackets which extend approximately at right angles to the plane of the plate and which have boreholes for screwing in bone screws (EP 298 233 A1 and EP 179 695 B1). However, the brackets and screw heads projecting beyond the front side of the vertebrae may endanger the blood vessels running immediately in front of the vertebrae.

The invention is based on the object of providing an intervertebral disc endoprosthesis of the type specified in the introduction, which avoids the said disadvantages and which can be securely anchored in the intervertebral space, especially even when there is pronounced lordosis.

The invention achieves this object by designing the facilities to receive the bone screws for a reception of the bone screws which runs essentially at right angles to the plane of the bottom or top plate in the front edge area of the bottom and/or top plate, and by displacing the center of articulation of the prosthesis towards the rear relative to the center of the vertebral endplates.

The displacement of the centre of articulation towards the rear reduces the forces which push the prosthesis towards the front as a result of the wedge-shaped opening of the vertebral space. At the same time, this measure provides space in the front area of the prosthesis for the facilities to receive the bone screws, The invention has recognized that these two characterising features of cooperate particularly beneficially for the purpose of prosthesis fixation. On the one hand, the force acting on the prosthesis in the direction of the ventral edge is reduced and, on the other hand, secure fixation is achieved without endangering the blood vessels which run immediately in front of the vertebrae.

The statement "at right angles to the plane of the plates" in the claims and the description is intended to embrace every direction which is able to include, relative to the plate, a screw cooperating with the plate or a borehole provided in the plate. Preferably it does not differ by more than 30° from a right angle to the plane of the bottom or top plate. Thus, a somewhat inclined course of a bone screw relative to the plane of the plate is also possible within the scope of the invention and may be particularly expedient when the bone screw is screwed in relatively close to the ventral edge of the vertebrae. It is then expediently screwed in with somewhat of an inclination towards the center of the vertebra.

It usually suffices to provide the screw fixation merely on the bottom plate or the top plate. The facilities to receive the bone screws are arranged on the front (ventral) edge of at least one of the plates of the prosthesis because this is where, owing to the displacement of the center of articulation towards the rear, there is most space available, and this area is most accessible. However, it is also possible within the scope of the invention to arrange the facilities to receive the bone screws in the lateral areas of the front edge of the plate. The facilities to receive the bone screws are expediently designed as borehole running essentially at right angles to the plane of the plates. Occasionally, a recess which is open towards the edge on the plate, which cooperates with the fastening screw and moreover prevents a displacement in a forward or inclined forward direction of the prosthesis also suffices. In any event, displacement towards the rear is usually not to be expected. The boreholes or recesses can also be arranged in special brackets which project in the plane of the prosthesis plates beyond the edge thereof. They may, in a manner known per se, have shapes or profiles such that they wholly or partly receive the screw heads so that the latter do not project. They can also be adapted to a particular screwing direction.

It is expedient for a bottom or top plate to have a plurality of screw fastenings which can, in particular, be provided in a paired symmetrical arrangement.

Figure 2:
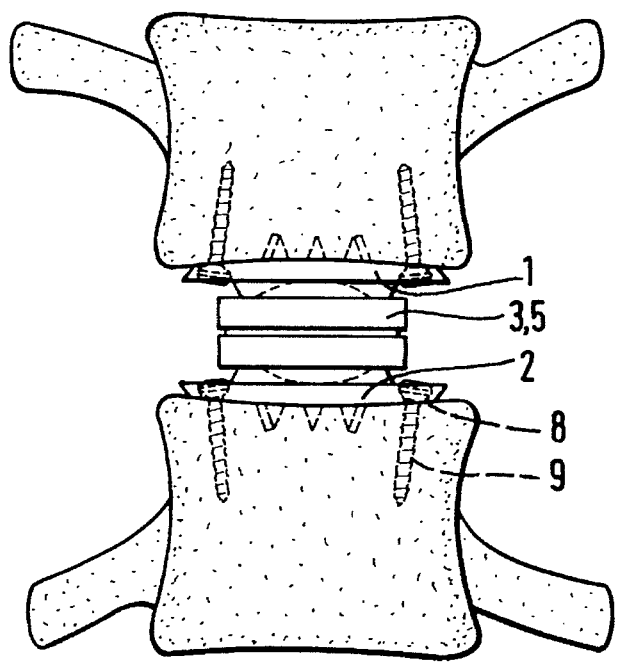
Figure 3:
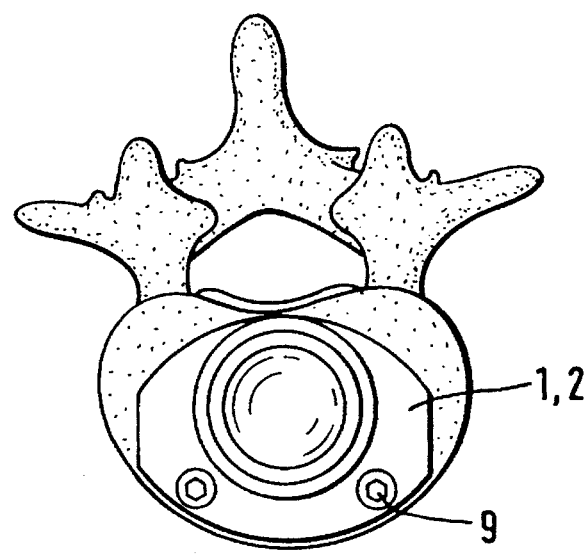
Figure 4:
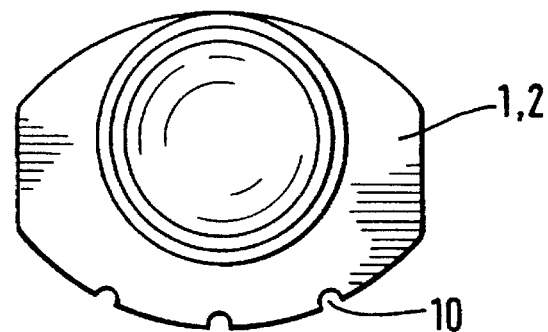
Figure 5:
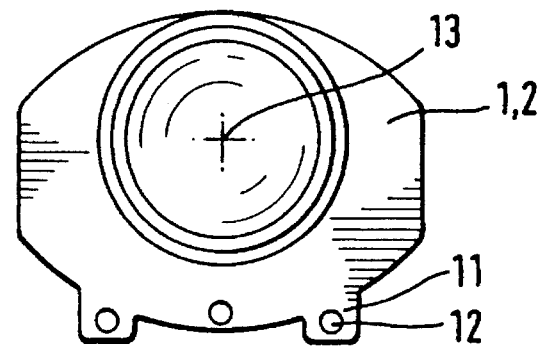

The invention is explained in detail hereinafter with reference to the drawing which illustrates advantageous exemplary embodiments. In this:

FIG. 1 shows a median section of a first embodiment of the prosthesis between two vertebrae, FIG. 2 shows a corresponding view from the front, FIG. 3 shows a plan view of the top plate of the prosthesis on the vertebra, FIG. 4 shows a plan view of a second embodiment of the prosthesis plate with screw recesses open towards the edge, and FIG. 5 shows a third embodiment in which the screw openings are arranged in brackets.

The prosthesis consists of a top plate 1 and of a bottom plate 2 which are designed as coincident mirror images and consist of metal and enclose between them a prosthesis core 3 made of polyethylene. The prosthesis plates 1, 2 and the prosthesis core 3 cooperate via spherical articular surfaces 4. The core 3 has an edge rim 5 which limits its range of movement and ensures, even under extreme conditions, cohesion of the prosthesis. The core can, in another embodiment, be rigidly connected to one of the plates.

The endplates 6 of the prosthesis plates 1,2 lie on the end surfaces of the vertebrae. They are provided with a number (for example six) of teeth 7 which, under load, penetrate into the vertebrae and thus secure the prosthesis in situ.

In the first embodiment according to FIG. 1, 2 and 3, boreholes 8 are arranged symmetrically on both sides of the central plane, running from ventral to dorsal, of the vertebrae and in the area of the front edge of the prosthesis plates 1, 2 to receive bone screws 9. The boreholes 8 and, correspondingly, also the screws 9 run at right angles to the plane of the prosthesis plates 1, 2.

The displacement of the center of articulation of the prosthesis towards the rear relative to the center of the vertebral endplates is evident from FIG. 3. This displacement provides sufficient space in the ventral edge area of the prosthesis plates 1, 2 to receive the bone screws 9.

In the embodiment according to FIG. 4, the boreholes for the bone screws are displaced into the edge area of the prosthesis plate 1, 2 so that they have become notches or indentations 10 which are open towards the edge. This saves space compared with the embodiment according to FIGS. 1 to 3, which is accordingly available for a larger forcetransmitting area. The recesses which are open towards the edge usually suffice to fix the prosthesis because there are not expected to be forces which might displace the prosthesis towards the rear.

Finally, it is also possible according to the embodiment depicted in FIG. 5 for the boreholes 12 for the bone screws to be provided in special brackets 11 which project towards the front in the plane of the prosthesis plates 1, 2. This arrangement is particularly suitable in cases in which a large displacement of the centre of articulation 13 towards the rear is intended.

I claim:

1. An intervertebral disc endoprosthesis for insertion in a vertebral space between two confronting vertebrae to permit substantially full natural movement of the confronting vertebrae, the endoprosthesis comprising a bottom plate, a top plate parallel to the bottom plate and facing in an opposite direction therefrom, end an intermediate core having an articular surface defining a center of articulation of the endoprosthesis, each plate having a front edge, a rear edge, and an outer surface configured to be positioned within the vertebral space and to bear against one of the two confronting vertebrae, at least one of the bottom and the top plates having means along the front edge for receiving at least one bone screw, said screw receiving means being arranged for positioning within the vertebral space and being configured to receive said bone screw at an angle that is within about thirty degrees of a right angle relative to the outer surface of the plate that also is positioned within the vertebral space, said articular surface of said endoprosthesis providing multidirectional articulation including rotation of the adjacent vertebrae and said center of articulation being spaced substantially from but displaced towards the rear edges of the plates.

2. Intervertebral disc endoprosthesis according to claim 1, characterised in that said means for receiving at least one bone screw comprise at least one borehole running at a right angle to the outer surface of the plate that is positioned within the vertical space.

3. An intervertebral disc endoprosthesis to be inserted in a vertebral space between two vertebrae having opposed end surfaces, the endoprosthesis permitting substantially full natural movement of the adjacent vertebrae and comprising a bottom plate, a generally parallel, oppositely facing top plate, and an intermediate core having an articular surface defining a center of articulation of the endoprosthesis, each plate having an outer surface configured to be positioned within the vertebral space and to bear against the end surface of one of the two vertebrae, a ventral edge, a rear edge, and a central portion, the ventral edge of at least one of the plates including means for receiving at least one bone screw at an angle which is within about thirty degrees of an axis which is normal to the outer surface of the plate, the screw receiving means being positioned within the vertebral space, said articular surface of the endoprosthesis providing multidirectional articulation including rotation of the adjacent vertebrae and said center of articulation being spaced substantially from but displaced toward the rear edge of the endoprosthesis relative to the central portions of the plates.

4. An intervertebral disc endoprosthesis according to claim 3, wherein the means for receiving at least one bone screw comprises at least one bore.

5. An intervertebral disc endoprosthesis according to claim 4, wherein the at least one bore extends in a direction which is generally perpendicular to the outer surface of the plate.

6. The intervertebral disc endoprosthesis of claim 1 wherein said screw receiving means includes a pair of bore holes positioned adjacent the front edge of the plate on opposite sides of the center of articulation.

7. The intervertebral disc endoprosthesis of claim 3 wherein said screw receiving means includes a pair of bore holes positioned adjacent the ventral edge of the plate on opposite sides of the center of articulation.

* * * * *